United States Patent [19]

Curran et al.

[11] 4,011,229

[45] Mar. 8, 1977

[54] 8-AMINO-5,6,7,8-TETRAHYDROQUINO-LINE DERIVATIVES

[75] Inventors: Adrian Charles Ward Curran, South Cave; Roger Crossley, Reading; David George Hill, Cookham, all of England

[73] Assignee: John Wyeth & Brother Limited, Maidenhead, England

[22] Filed: Apr. 2, 1976

[21] Appl. No.: 673,016

Related U.S. Application Data

[63] Continuation-in-part of Ser. No. 554,259, Feb. 28, 1975, Pat. No. 3,991,065.

[30] Foreign Application Priority Data

Mar. 5, 1974 United Kingdom ............. 9763/74

[52] U.S. Cl. .................. 260/288 R; 260/283 S; 260/283 R; 260/287 T; 260/289 XA; 424/274
[51] Int. Cl.² ..................................... C07D 215/40
[58] Field of Search ............................. 260/288 R

[56] References Cited

UNITED STATES PATENTS

| | | | |
|---|---|---|---|
| 3,426,026 | 2/1969 | Ennis et al. | 260/288 R |
| 3,860,599 | 1/1975 | Covelli | 260/288 R |

OTHER PUBLICATIONS

Poludnenko et al., Chem. Abst. vol. 74:53657d, (1971).

*Primary Examiner*—Donald G. Daus
*Assistant Examiner*—Mary C. Vaughn

[57] ABSTRACT

The invention provides 5,6,7,8-tetrahydroquinoline derivatives which are substituted at the 8-position by an amino group. The 8-amino compounds are intermediates for corresponding thiocarbamoyl derivatives which are anti-ulcer agents.

4 Claims, No Drawings

8-AMINO-5,6,7,8-TETRAHYDROQUINOLINE DERIVATIVES

This application is a continuation-in-part of our co-pending U.S. application Ser. No. 554,259 filed Feb. 28, 1975, now Pat. No. 3,991,065.

The invention relates to novel tetrahydroquinoline derivatives and to processes for preparing them.

The invention provides a compound of formula I

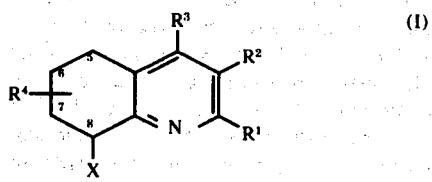

and pharmaceutically acceptable acid addition salts thereof, wherein $R^1$, $R^2$ and $R^3$ are the same or different and represent hydrogen, or lower alkyl of 1–6 carbon atoms, $R^4$ represents hydrogen or substitution at the 5,6 or 7-position by lower alkyl of 1–6 carbon atoms and X is amino, with the proviso that when any two of $R^1$, $R^2$ and $R^3$ are lower alkyl and are on adjacent carbon atoms then they are selected from normal and secondary alkyl groups.

When any of $R^1$, $R^2$, $R^3$ or $R^4$ is a lower alkyl group it has from 1 to 6 carbon atoms and may have a straight or branched chain, e.g. methyl, ethyl, n-, and iso-propyl and n-, s- and t-butyl, $R^4$ may be a gem-dimethyl group.

A preferred group of compounds have formula

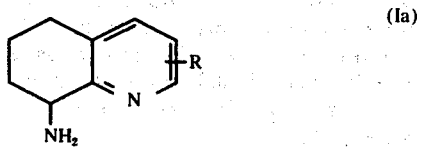

where R is hydrogen or lower alkyl of 1–6 carbon atoms.

Particularly preferred compounds of formula I ar those in which at least one or more of $R^1$, $R^2$, $R^3$ and $R^4$ is methyl and the others are hydrogen.

Compounds of formula I wherein X is amino are intermediates for corresponding compounds where X is NHCSNHR[5], wherein R[5] is hydrogen, or alkyl of 1–3 carbon atoms which compounds are anti-ulcer agents possessing activity in the anti-ulcer test of Brodie and Hanson (see below) and sometimes anti-secretory or gastric anti-histamine activity in the test of Shay et al (see below). Compounds where R[5] is alkyl of 1–3 carbon atoms generally have anti-secretory activity. R[5] may be methyl, ethyl or n-propyl.

The compounds of formula I and Ia can form acid addition salts with inorganic acids e.g. hydrochloric, hydrobromic, sulphuric or nitric acids, or organic acids, e.g. citric, fumaric, maleic or tartaric acids. These acid addition salts are included in the invention.

In the compounds of formula I and Ia the carbon atom to which X is attached is asymmetric. Consequently, the compounds can exist in optically active d and l forms. These optically active forms and the racemates are included in the invention. The optically active forms may be separated by standard techniques.

The compounds of formula I and Ia where X is amino may be used for preparing compounds of formula I wherein X is NHCSNHR[5] and R[5] is alkyl of 1–3 carbon atoms; or aroyl or alkanoyl by reacting a compound of formula I wherein X is amino with an isothiocyanate of formula R[5]NCS wherein R[5] is as just defined.

The products wherein R[5] is aroyl or alkanoyl are useful intermediates for preparing corresponding compounds wherein R[5] is hydrogen. Thus a process for preparing compounds of formula I wherein X is NHCSNH$_2$ comprises hydrolysing a corresponding compound of formula I wherein X is NHCSNH Acyl.

When R[5] is aroyl it may be a benzoyl or substituted benzoyl radical e.g. halobenzoyl, such as chlorobenzoyl. When R[5] is lower alkanoyl it may have from 2 to 7 carbon atoms examples being acetyl, propionyl, butyryl, and hexanoyl.

The hydrolysis of a compound where R[5] is aroyl or lower alkanoyl may be carried out by treatment with a suitable base e.g. an alkali or alkaline earth metal hydroxide. Conveniently, sodium or potassium hydroxide may be used.

Processes for preparing the compounds of formula I wherein X is amino are also included in the invention. They may be prepared by treatment of corresponding compounds of formula I wherein X is chloro or bromo with ammonia in a lower alkanol, e.g. methanol or ethanol.

This method is also included in the invention. The compounds of formula I wherein X is chloro or bromo are either known compounds or if novel may be prepared by methods analogous to the preparation of known compounds e.g. by treatment of a corresponding compound of formula I wherein X is hydroxy with thionyl chloride or phosphorus trichloride or tribromide, or by treatment of an N-oxide of a compound of formula I wherein X is hydrogen with an alkyl sulphonyl halide e.g. Me SO$_2$Cl.

The starting materials wherein X is hydroxy are either known compounds or if novel may be prepared by methods known for analogous compounds e.g. by formation of the N-oxide of a compound of formula I, wherein X is hydrogen with hydrogen peroxide, followed by acylation of the N-oxide and hydrolysis to give the compound of formula I wherein X is hydroxy.

A further method for preparing the compounds of formula I wherein X is amino comprises reducing a corresponding oxime of formula I, wherein X is =0 NOH. The oximes may be prepared by treatment of a corresponding compound of formula I, wherein X is oxo with hydroxylamine or by treatment of a corresponding compound of formula I wherein X is hydrogen with isoamyl nitrate in the presence of butyl lithium.

An alternative method for preparing compounds of formula I wherein R[5] is hydrogen comprises reacting a compound of formula I wherein X is NH$_2$ with a compound of formula R$_x$Si(NCS)$_{4-x}$ wherein R is an alkyl, aryl or aralkyl radical or Rx is any mixture of these and x is 0,1,2 or 3 and then subjecting the product to hydrolysis or alcoholysis.

Examples of the compound R$_x$Si(NCS)$_{4-x}$ are x=0 : Si(NCS)$_4$; x = 1 : RSi(NCS)$_3$; x = 2: R$_2$Si(NCS)$_2$; and x = 3: R$_3$SiNCS, wherein R has any of the meanings given above.

When x is 3 the radical R$_x$ may be a tri-alkyl, tri-aryl or tri-aralkyl and is preferably a tri-loweralkyl e.g. trimethyl.

The reaction with the compound of formula $R_xSi(NCS)_{4-x}$ is conducted under anhydrous conditions, preferably in an inert solvent, for example a hydrocarbon solvent such as benzene, toluene or hexane. Ethers including cyclic ethers such as tetrahydrofuran should be avoided. The product of the first stage of the reaction is a compound of formula I wherein $R^5$ is $SiR_x(NCS)_{3-x}$.

These intermediate compounds are not usually isolated.

The desired compound of formula I wherein $R^5$ is hydrogen is conveniently formed by treating the above intermediate with water or a lower alkanol e.g. ethanol.

The compounds of formula I, wherein X is $NHCSNHR^5$ wherein $R^5$ is hydrogen, or alkyl of 1–3 carbon atoms, are anti-ulcer agents which display one or more of the following activities:anti-ulcer, anti-secretory or gastric anti-histamine activity. Anti-ulcer activity is determined by the method of Brodie and Hanson, J. Applied Physiology, 15, 291, 1960.

Anti-secretory activity and gastric anti-histamine activity are determined by the method of H. Shay, D. Sun and H. Greenstein, Gastroenterology 1954, 26, 906–13. Activity in one or more of the above tests denotes an anti-ulcer agent.

The invention is illustrated by the following Examples. Temperatures are in ° C.

EXAMPLE 1

8-Hydroxy-3-methyl-5,6,7,8-tetrahydroquinoline

3-Methyl-5,6,7,8-tetrahydroquinoline (50 g.) was dissolved in glacial acetic acid (180 ml.) and the solution treated with 30% hydrogen peroxide (70 ml.) and heated at 80° C for 20 hours. The solvent was removed in vacuo and the residual oil diluted with water (25 ml.) and re-evaporated. The resulting oil was dissolved in chloroform (100 ml.), washed with aqueous sodium carbonate (2 × 25 ml.), saturated brine (2 × 25 ml.), dried (MgSO$_4$) and the solvent removed in vacuo to give 3-Methyl-5,6,7,8-tetrahydroquinoline-1-oxide (60 g.) as a pale yellow solid which was used without purification.

The N-oxide (60 g.) was dissolved in acetic anhydride (120 ml.) and added to boiling acetic anhydride (120 ml.) and the mixture heated at reflux for 30 minutes. The solvent was removed in vacuo and the residual oil was treated with 10% hydrochloric acid (700 ml.) and the solution heated on a steam bath for 2 hours. The cooled reaction mixture was adjusted to pH 9.0 with sodium hydroxide and extracted with ether (3 × 100 ml). The combined ethereal extracts were washed with saturated brine, dried (MgSO$_4$) and the solvent removed in vacuo. The resultant oil as distilled at 0.15 mmHg to give a colourless oil (22 g.) b.p. 70°–78° C which crystallised from n-hexane to give 8-hydroxy-3-methyl-5,6,7,8-tetrahydroquinoline as colourless needles m.p. 58° C.

(Found: C,73.7; H, 8.2; N, 8.3. $C_{10}H_{13}NO$ requires: C 73.6; H, 8.0 N, 8.6%)

EXAMPLE 2

8-Chloro-3-methyl-5,6,7,8-tetrahydroquinoline

The 8-hydroxy product of Example 1 (15 g.) was added portionwise to thionyl chloride (33 g.) at 0° C and the mixture stirred at 0° C for 1 hour and heated at reflux for an additional 2 hours. The solvent was removed in vacuo and the residual oil heated at reflux for 1 hour with ethanol (15 ml.) to remove excess thionyl chloride. The resultant precipitate was recrystallised from ethanolether to give 8-chloro-3-methyl-5,6,7,8-tetrahydroquinoline hydrochloride as colourless needles (17.4 g.) m.p. 177° C.

(Found: C, 55.3; H, 6.1 N, 6.5. $C_{10}H_{12}ClN.HCl$ requires C, 55.1; H, 6.0 N, 6.4%).

EXAMPLE 3

8-Amino-3-methyl-5,6,7,8-tetrahydroquinoline

The 8-chloro product of Example 2 (17 g.) was dissolved in methanol saturated with ammonia (400 ml.) and heated at 80° in a stainless steel bomb for 24 hours. The solvent was removed in vacuo and the residual oil triturated with anhydrous ether (3 × 50 ml.) and the triturates discarded. The oily solid was dissolved in water and the pH adjusted to 9.0 with sodium carbonate and extracted with ether (3 × 150 ml.). The combined extracts were dried (MgSO$_4$) and the solvent removed in vacuo to give a pale yellow oil (5.5 g.). A sample (500 mg.) was dissolved in anhydrous ether (25 ml.) and the solution treated with excess ethereal hydrogen chloride and the resultant solid recrystallised from methanol-ether to give 8-amino-3-methyl-5,6,7,8-tetrahydroquinoline dihydrochloride quarter hydrate as colourless needles m.p. 210° C.

(Found: C. 50.5; H, 6.9; N, 11.6. $C_{10}H_{14}N_2$. 2HCl. 1/4H$_2$O requires: C, 50.2; H, 7.1; N, 11.7%).

EXAMPLE 4

8-Methylthiocarbamoylamino-3-methyl-5,6,7,8-tetrahydroquinoline

The 8-amino product of Example 3 (free base) (3 g) was dissolved in acetonitrile (30 ml.) and the solution treated with methylisothiocyanate (1.35 g.) and heated at reflux for 2 hours. The solvent was removed in vacuo and the residual solid recrystallised from absolute ethanol to give the title compound as colourless needles (3 g.) m.p. 113° C.

(Found: C, 61.4; H, 7.3; N, 17.8; $C_{12}H_{17}N_3S$ requires: C, 61.2; H, 7.3; N, 17.9%).

The product displayed anti-ulcer activity in the test of Brodie & Hanson (loc. cit.), and anti-secretory and gastric anti-histamine activity in the test of Shay et al (loc. cit.).

EXAMPLE 5

8-Benzoylthiocarbamoylamino-3-methyl-5,6,7,8-tetrahydroquinoline

A solution of 8-amino-3-methyl-5,6,7,8-tetrahydroquinoline (6 g.) in acetone (48 ml.) was treated with benzoylisothiocyanate (6 g.) and the mixture heated at reflux for 45 minutes. The solvent was removed in vacuo and the residual solid recrystallised from ethanol-ether to give the title compound as colourless needles (7.2 g.) m.p. 168° C.

(Found: C, 66.5; H, 6.1; N, 13.0. $C_{18}H_{19}N_3OS$ requires: C, 66.4; H, 5.9; N, 12.9%).

EXAMPLE 6

8-Thiocarbamoylamino-3-methyl-5,6,7,8-tetrahydroquinoline

8-Benzoylthiocarbamoylamino-3-methyl-5,6,7,8-tetrahydroquinoline (6 g.) was treated with a 10% sodium hydroxide solution (24 ml.) and the mixture heated on a steam bath for 15 minutes. The cooled reaction mixture was adjusted to pH 1.0 with conc. HCl, filtered to remove benzoic acid and the filtrate adjusted to pH 10.0 with aqueous ammonia. The resultant solid was recrystallised from ethanol to give the hydrate of the title compound as colourless needles (4 g.).m.p. 114° C.

(Found C, 55.3; H, 7.3; N, 17.2. $C_{11}H_{15}N_3S.H_2O$ requires: C, 55.1; H, 7.3; N, 17.4%).

The product displayed anti-ulcer activity in the test of Brodie & Hanson (loc.cit.).

EXAMPLE 7

8-Chloro-3-methyl-5,6,7,8-tetrahydroquinoline

Methanesulphonyl chloride (1.62 ml., 0.02 mol.) was added dropwise at 0° C to 3-methyl-5,6,7,8-tetrahydroquinoline-1-oxide (1.63 g., 0.02 mol.) and the mixture stirred at 0° C for 2 hours and at 80° C for 2.5 hours. The cooled reaction mixture was diluted with water (5 ml.) and the pH adjusted to 9.0 with sodium carbonate and the solution extracted with ethyl acetate (3 × 25 ml.).

The combined extracts were dried ($MgSO_4$) and the solvent removed in vacuo to give a yellow oil (1.2 g.). A sample (500 mg.) was dissolved in anhydrous ether and treated with excess ethereal hydrogen chloride and the resultant solid recrystallised from ethanol-ether to give the title compound as colourless needles. m.p. 177° C identical to authentic material.

EXAMPLE 8

3-Methyl-8-oximino-5,6,7,8-tetahydroquinoline

8-Hydroxy-3-methyl-5,6,7,8-tetrahydroquinoline (42.5g) in methylene chloride (2½l) was stirred at room temperature with manganese dioxide (425g) for 16 hours. The manganese dioxide was removed by filtration and washed with methylene chloride. The filtrate was evaporated to dryness under reduced pressure and the residue was distilled to give 5,6-dihydro-3-methyl-7H-quinolin-8-one (30g) b.p. 142°–4° C at 0.5mm.

The quinolinone (30g), hydroxylamine hydrochloride (14g), sodium hydroxide (9g), ethanol (165ml) and water (65ml) were stirred and refluxed for 2 hours. Water (100 ml) was added and the product was allowed to crystallise overnight. The crystals were removed by filtration and washed with water and dried to give 3-methyl-8-oximino-5,6,7,8-tetrahydroquinoline (27.5g) mp 188° C.

(Found: C, 68.5; H 6.9; N, 15.4, $C_{10}H_{12}N_2O$ requires C, 68.2; H, 6.9; N, 15.1%.

EXAMPLE 9

8-Amino -3-methyl-5,6,7,8,-tetrahydroquinoline

3-Methyl-8-oximino-5,6,7,8-tetrahydroquinoline (27.5g) was dissolved in ethanol (550ml) and 2N sodium hydroxide solution (550ml) was added. The solution was stirred vigorously and nickel aluminium alloy (41.3g) was added portionwise over 30 mins and the mixture was stirred at room temperature for 2 hours. The reaction mixture was filtered through kieselguhr and the filter cake washed with ethanol and water. The combined filtrate was evaporated to low bulk under reduced pressure and the residue was extracted with chloroform. The chloroform solution was dried ($MgSO_4$) and evaporated under reduced pressure. The residue was dissolved in ether (500ml) and filtered and ethereal HCl was added to the filtrate till no more precipitate formed. The solid was removed by filtration and recrystallised from mthanol/ether to give 8-amino-3-methyl-5,6,7,8-tetrahydroquinoline hydrochloride (26.2g).

EXAMPLE 10

4-Methyl-8-oximino-5,6,7,8-tetrahydroquinoline

Following the procedure of Examples 1 and 8 4-methyl-5,6,7,8-tetrahydroquinoline may be converted to 4-methyl-8-oximino-5,6,7,8-tetrahydroquinoline.

EXAMPLE 11

8-Amino-4-methyl-5,6,7,8-tetrahydroquinoline

Following the procedure of Example 9 4-methyl-8-oximino-5,6,7,8-tetrahydroquinoline may be converted to 8-amino-4-methyl-5,6,7,8-tetrahydroquinoline which may be obtained as the hydrochloride in the manner of Example 9.

EXAMPLE 12

8-Methylthiocarbamoylamino-4-methyl-5,6,7,8-tetrahydroquinoline

The title compound may be obtained from the 8-amino compound of Example 11 by following the procedure of Example 4.

EXAMPLE 13

3,7,7-Trimethyl-8-oximino-5,6,7,8-tetrahydroquinoline 3,7,7-Trimethyl-5,6,7,8-tetrahydroquinoline may be converted to the title compound by following the procedure of Examples 1 and 8.

EXAMPLE 14

8-Amino-3,7,7-trimethyl-5,6,7,8-tetrahydroquinoline

The oxime of Example 13 may be converted to the title compound by the procedure of Example 9.

EXAMPLE 15

8-Methylthiocarbamoylamino-3,7,7-trimethyl-5,6,7,8-tetrahydroquinoline

The title compound may be prepared by treating the amino compound of Example 14 with methylisothiocyanate according to the procedure of Example 4.

EXAMPLE 16

2-Ethyl-8-oximino-5,6,7,8-tetrahydroquinoline

2-Ethyl-5,6,7,8-tetrahydroquinoline may be converted to the title compound by following the procedures of Examples 1 and 8.

EXAMPLE 17

8-Amino-2-ethyl-5,6,7,8-tetrahydroquinoline

The product of Example 16 may be converted to the title compound by following the procedure of Example 9.

EXAMPLE 18

2-Ethyl-8-methylthiocarbamoylamino-5,6,7,8-tetrahydroquinoline

The amino compound of Example 17 may be converted to the title compound by treatment with methylisothiocyanate according to the procedure of Example 4.

EXAMPLE 19

2-n-Butyl-8-oximino-5,6,7,8-tetrahydroquinoline 2-n-Butyl-5,6,7,8-tetrahydroquinoline may be converted to the title compound following the procedures of Examples 1 and 8.

EXAMPLE 20

8-Amino-2-n-butyl-5,6,7,8-tetrahydroquinoline

The 8-oxime of Example 19 may be converted to the 8-amino title compound by the procedure of Example 9.

EXAMPLE 21

2-n-Butyl-8-methylthiocarbamoylamino-5,6,7,8-tetrahydroquinoline

The product of Example 20 may be converted to the title compound by the procedure of Example 4.

EXAMPLE 22

8-Oximino-2-phenyl-5,6,7,8-tetrahydroquinoline

2-Phenyl-5,6,7,8-tetrahydroquinoline may be converted to the title compound following the procedures of Examples 1 and 8.

EXAMPLE 23

8-Amino-2-phenyl-5,6,7,8-tetrahydroquinoline

The 8-oxime product of Example 22 may be converted to the title compound following the procedure of Example 9.

EXAMPLE 24

8-Methylthiocarbamoylamino-2-phenyl-5,6,7,8-tetrahydroquinoline

The 8-amino-compound of Example 23 may be treated with methylisothiocyanate to give the title compound following the procedure of Example 4.

EXAMPLE 25

Following the procedure of Examples 1 and 8 the indicated 5,6,7,8-tetrahydroquinolines may be converted to the corresponding 8 oximes

| 5,6,7,8-tetrahydroquinoline (THQ) derivative | |
|---|---|
| Starting material | Final Product (THQ) |
| 3,4-dimethyl-THQ | 3,4-dimethyl-8-oximino-THQ |
| 3,5-dimethyl-THQ | 3,5-dimethyl-8-oximino-THQ |
| 3,6-dimethyl-THQ | 3,6-dimethyl-8-oximino-THQ |
| 2,4-dimethyl-THQ | 2,4-dimethyl-8-oximino-THQ |
| 3-n-butyl-THQ | 3-n-butyl-8-oximino-THQ |
| 3-n-pentyl-THQ | 8-oximino-3-n-pentyl-THQ |
| 3,7-dimethyl-THQ | 3,7-dimethyl-8-oximino-THQ |
| 5-n-butyl-3-methyl-THQ | 5-n-butyl-3-methyl-8-oximino-THQ |
| 3-methyl-6-isopropyl-THQ | 3-methyl-8-oximino-6-isopropyl-THQ |
| 4-n-hexyl-THQ | 4-n-hexyl-8-oximino-THQ |
| 5-methyl-THQ | 5-methyl-8-oximino-THQ |
| 6-ethyl-THQ | 6-ethyl-8-oximino-THQ |
| 7-n-propyl-THQ | 8-oximino-7-n-propyl-THQ |

EXAMPLE 26

Following the procedure of Example 9 the indicated 8-oximes may be converted to the indicated 8-amino compounds which in turn may be converted to the indicated 8-methylthiocarbamoylamino-5,6,7,8-tetrahydroquinolines by the procedure of Example 4.

| 5,6,7,8-tetrahydroquinoline (THQ) Derivative | | |
|---|---|---|
| Starting material | 8-amino-THQ | 8-methylthiocarbamoyl-THQ |
| 3,4-dimethyl-8-oximino-THQ | 8-amino-3,4-dimethyl-THQ | 3,4-dimethyl-8-methyl-thiocarbamoylamino-THQ |
| 3,5-dimethyl-8-oximino-THQ | 8-amino-3,5-dimethyl-THQ | 3,5-dimethyl-8-methyl-thiocarbamoylamino-THQ |
| 3,6-dimethyl-8-oximino-THQ | 8-amino-3,6-dimethyl-THQ | 3,6-dimethyl-8-methyl-thiocarbamoylamino-THQ |
| 2,4-dimethyl-8-oximino-THQ | 8-amino-2,4-dimethyl-THQ | 2,4-dimethyl-8-methyl-thiocarbamoylamino-THQ |
| 3-n-butyl-8-oximino-THQ | 8-amino-3-n-butyl-THQ | 3-n-butyl-8-methyl-thiocarbamoylamino-THQ |
| 3-n-pentyl-8-oximino-THQ | 8-amino-3-n-pentyl-THQ | 8-methylthiocarbamoyl-amino-3-n-pentyl-THQ |
| 3,7-dimethyl-8-oximino-THQ | 8-amino-3,7-dimethyl-THQ | 3,7-dimethyl-8-methyl-thiocarbamoylamino-THQ |
| 5-n-butyl-3-methyl-8-oximino-THQ | 8-amino-5-n-butyl-3-methyl-THQ | 5-n-butyl-3-methyl-8-methylthiocarbamoyl-amino-THQ |
| 3-methyl-8-oximino-6-iso-propyl-THQ | 8-amino-3-methyl-6-isopropyl-THQ | 3-methyl-8-methylthio-carbamoylamino-6-iso-propyl-THQ |
| 4-n-hexyl-8-oximino-THQ | 8-amino-4-n-hexyl-THQ | 4-n-hexyl-8-methylthio-carbamoylamino-THQ |
| 5-methyl-8-oximino-THQ | 8-amino-5-methyl-THQ | 5-methyl-8-methyl-thiocarbamoylamino-THQ |
| 6-ethyl-8-oximino-THQ | 8-amino-6-ethyl-THQ | 6-ethyl-8-methylthio-carbamoylamino-THQ |
| 8-oximino-7-n-propyl-THQ | 8-amino-7-n-propyl THQ | 8-methylthiocarbamoyl-amino-7-n-propyl-THQ |

EXAMPLE 27

Following the procedure of Example 5, the following compounds may be prepared from 8-amino-3-methyl-5,6,7,8-tetrahydroquinoline by replacing benzoylisothiocyanate by the indicated isothiocyanate. The 8-acyl-thiocarbamoylamino compounds formed may be converted to 8-thiocarbamoylamino-3-methyl-5,6,7,8-tetrahydroquinoline by hydrolysis in the manner described in Example 6.

| Isothiocyanate | 8-acyl-thiocarbamoylamino tetrahydroquinoline-(THQ) |
|---|---|

| | -continued |
|---|---|
| acetylisothiocyanate | 8-acetylthiocarbamoylamino-3-methyl-THQ |
| propionylisothiocyanate | 3-methyl-8-propionylthiocarbamoylamino-THQ |
| p-chlorobenzoylisothiocyanate | 8-p-chlorobenzoylthiocarbamoyl-3-methylamino-THQ |

We claim:
1. A compound of formula I

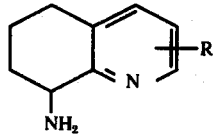

and pharmaceutically acceptable acid addition salts thereof, wherein $R^1$, $R^2$ and $R^3$ are the same or different and represent hydrogen, or lower alkyl of 1–6 carbon atoms, $R^4$ represents hydrogen or substitution at the 5,6 or 7-position by lower alkyl of 1–6 carbon atoms, with the proviso that when any two of $R^1$, $R^2$ and $R^3$ are lower alkyl and are on adjacent carbon atoms then they are selected from normal and secondary alkyl groups.

2. A compound of formula Ia (Ia)

wherein R is hydrogen or lower alkyl of 1–6 carbon atoms.

3. A compound as claimed in claim 1 wherein $R^1$, $R^2$, $R^3$ and $R^4$ are selected from hydrogen and methyl.

4. A compound as claimed in claim 1, which is 8-amino-3-methyl-5,6,7,8-tetrahydroquinoline or a pharmaceutically acceptable acid addition salt thereof.

* * * * *

UNITED STATES PATENT OFFICE
CERTIFICATE OF CORRECTION

PATENT NO. : 4,011,229
DATED : March 8, 1977
INVENTOR(S) : Adrian Charles Ward Curran, Roger Crossley, David George Hill It is certified that error appears in the above-identified patent and that said Letters Patent are hereby corrected as shown below:

Col. 1, line 45 "ar" should be "are".

Col. 2, line 48 delete "O".

Col. 2, line 53 "nitrate" should be "nitrite".

Col. 6, line 3 "methanol" is misspelled.

Signed and Sealed this fifth Day of July 1977

[SEAL]

Attest:

RUTH C. MASON
*Attesting Officer*

C. MARSHALL DANN
*Commissioner of Patents and Trademarks*